US009652710B2

(12) United States Patent
Voillat (10) Patent No.: US 9,652,710 B2
(45) Date of Patent: May 16, 2017

(54) METHOD FOR RECORDING THE NUMBER OF STERILIZATIONS OF A PIECE FOR A MEDICAL DEVICE

(71) Applicant: Dassym SA, Hauterive (CH)

(72) Inventor: Jean-Pierre Voillat, Montavon (CH)

(73) Assignee: DASSYM SA, Hauterive (CH)

( * ) Notice: Subject to any disclaimer, the term of this patent is extended or adjusted under 35 U.S.C. 154(b) by 67 days.

(21) Appl. No.: 14/636,559

(22) Filed: Mar. 3, 2015

(65) Prior Publication Data

US 2015/0254550 A1   Sep. 10, 2015

(30) Foreign Application Priority Data

Mar. 4, 2014   (CH) ........................................ 312/14

(51) Int. Cl.
| | |
|---|---|
| *G07C 3/00* | (2006.01) |
| *G01F 15/06* | (2006.01) |
| *G06M 3/08* | (2006.01) |
| *A61C 19/00* | (2006.01) |
| *A61L 2/26* | (2006.01) |
| *A61L 2/28* | (2006.01) |

(52) U.S. Cl.
CPC ............ *G06M 3/08* (2013.01); *A61C 19/002* (2013.01); *A61L 2/26* (2013.01); *A61C 2204/005* (2013.01); *A61L 2/28* (2013.01); *A61L 2202/14* (2013.01); *A61L 2202/24* (2013.01)

(58) Field of Classification Search
USPC ...................................................... 377/1–130
See application file for complete search history.

(56) References Cited

U.S. PATENT DOCUMENTS

| | | | | |
|---|---|---|---|---|
| 5,359,993 | A | 11/1994 | Slater et al. | |
| 6,611,793 | B1 * | 8/2003 | Burnside | ............ A61B 18/1206 128/897 |
| 8,600,374 | B1 * | 12/2013 | Hertlein | .................. H04M 1/18 455/425 |
| 2003/0106930 | A1 * | 6/2003 | Williams | ................ G06M 1/00 235/103 |
| 2013/0106369 | A1 * | 5/2013 | Arunachalam | .... G05B 19/0423 323/234 |
| 2015/0374868 | A1 * | 12/2015 | Bruce | ..................... A61L 2/208 422/3 |

OTHER PUBLICATIONS

International Search Report for CH 3122014 dated Jul. 8, 2014.

* cited by examiner

*Primary Examiner* — Brandon S Cole
(74) *Attorney, Agent, or Firm* — Pearne & Gordon LLP (57) ABSTRACT

A method for recording the number of sterilizations of a piece for a medical device. The piece can be a motor and/or a handpiece. The piece includes a temperature sensor and/or a pressure sensor and/or a humidity sensor and/or an angular position. The method includes the following steps: inserting the piece into the sterilization camber; detecting the sterilization based on the temperature and/or the pressure and/or the humidity and/or the angular position in which the handpiece is received in the sterilization chamber by the temperature sensor and/or the pressure sensor (102) and/or the humidity sensor and/or the angular position sensor. This solution allows recording of the number of sterilizations of a handpiece and/or a motor for a medical device, in particular for a dental device.

16 Claims, 6 Drawing Sheets

METHOD FOR RECORDING THE NUMBER OF STERILIZATIONS OF A PIECE FOR A MEDICAL DEVICE

The present application claims the priority of Swiss patent application CH2014-00312, filed on Mar. 4, 2014, the content of which is hereby incorporated by reference.

TECHNICAL FIELD OF THE INVENTION

The present invention concerns a method for recording the number of sterilizations of a piece for a medical device, in particular a dental device, for example a motor for a medical device, in particular a dental device. It concerns also a piece for a medical device, in particular a dental device.

BACKGROUND OF THE INVENTION

Surgical systems, in particular dental systems, comprise an instrument having a handpiece, for example a contra-angle, which may be provided with a tool, for example a milling cutter—and a rotating motor that drives the tool. The handpiece and the motor may be two separate pieces and interconnected by appropriate interfaces or may constitute a single piece. The controller device of the instrument is often connected to the patient's chair and connected to the manual instrument by a flexible connection containing electric wires and tubes for passing air and water.

This type of instrument needs to be sterilized regularly. The sterilization is usually performed by autoclaving, or in general, in a sterilization chamber.

The state of the art, however, has no solution for the traceability of sterilization activities such as counting the number of sterilizations. This traceability allows the after-sales service to have additional information on the surgical instrument, and also allows a secure use of instruments in hospitals.

BRIEF SUMMARY OF THE INVENTION

An aim of the present invention is to provide a method for recording the number of sterilizations of a motor and/or a handpiece for a medical device.

Another aim of the invention is to provide a motor and/or a handpiece for a medical device allowing this recording.

According to the invention, these aims are achieved in particular by means of a method for recording the number of sterilizations of a piece for a medical device, in particular for a dental device, said piece being a motor and/or a handpiece, said piece comprising a temperature sensor and/or a pressure sensor and/or a humidity sensor and/or an angular position sensor that said piece has when placed in a sterilization chamber, said method comprising the following steps:

inserting said piece into the sterilization chamber;
  detecting of the sterilization based on said temperature and/or said pressure and/or said humidity and/or said angular position sensed in said sterilization chamber (10) by said temperature sensor and/or said pressure sensor (102) and/or said humidity sensor and/or said angular position sensor The invention also relates to a piece (motor and/or handpiece) for a medical device, in particular for a dental device, for the implementation of the method according to the invention.

This solution has the particular advantage over the prior art to allow to record the number of sterilizations of a motor and/or of a handpiece for a medical device.

BRIEF DESCRIPTION OF THE DRAWINGS

Examples of implementation of the invention are indicated in the description that is illustrated by the annexed figures.

DETAILED DESCRIPTION OF POSSIBLE EMBODIMENTS OF THE INVENTION

In the following description that is provided as example, we will refer, for simplicity, to a motor for a device or surgical instrument, in particular for a dental instrument. However, it should be understood that the invention is not limited to a motor, but also refers to a handpiece, which can be separated from the motor, or forms a single piece with the motor.

Sterilization of a motor for a surgical device is generally performed in a sterilization chamber, for example an autoclave.

Four physical quantities characterize such sterilization:
Temperature: 120° C.-134° C.
Humidity: 100%
Time: 2 minutes-20 minutes
Pressure: 50 mbar-2.2 bar.

To detect and memorize a phenomenon, it is necessary to have at disposal a minimum of energy. During the sterilization, the motor is completely disconnected and deprived of any energy. It is therefore imperative that an energy source is present during sterilization. So there are two possible solutions:
1. Sensing in the "atmosphere" of sterilization, i.e., in the sterilization chamber, a physical quantity capable of generating recoverable information when the motor is putting back into service.
2. Equipping the motor with a battery that can power an embedded microprocessor in response of a "wake up" signal that is responsive to a physical quantity of sterilization.

There are three types of motors for medical devices, including surgical, for example dental devices:
  motors equipped with a microprocessor;
  motors equipped with an electronic rotor position measurement, but devoid of microprocessor;
  sensorless motors, i.e. devoid of sensors, that are devoid of microprocessor and electronics for the rotor position measurement.

Figure 1:
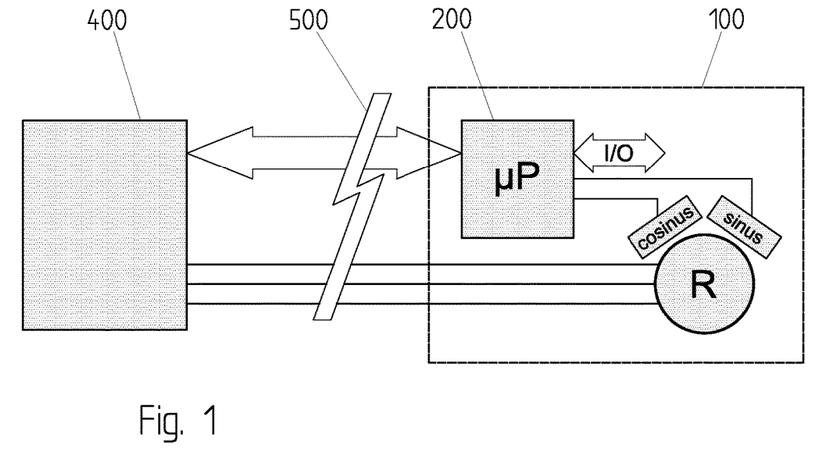
FIG. 1 illustrates an example of a motor equipped with a microprocessor, and allowing an API communication ("Application Programming Interface") with a control electronic.

FIG. 1 illustrates an example of motor 100 equipped with a microprocessor 200, that allows an API ("Application Programming Interface") communication, indicated by the double arrow, with an electronic control unit 400. An example of such a motor is described in the application CH706607, filed by the Applicant.

Figure 2:
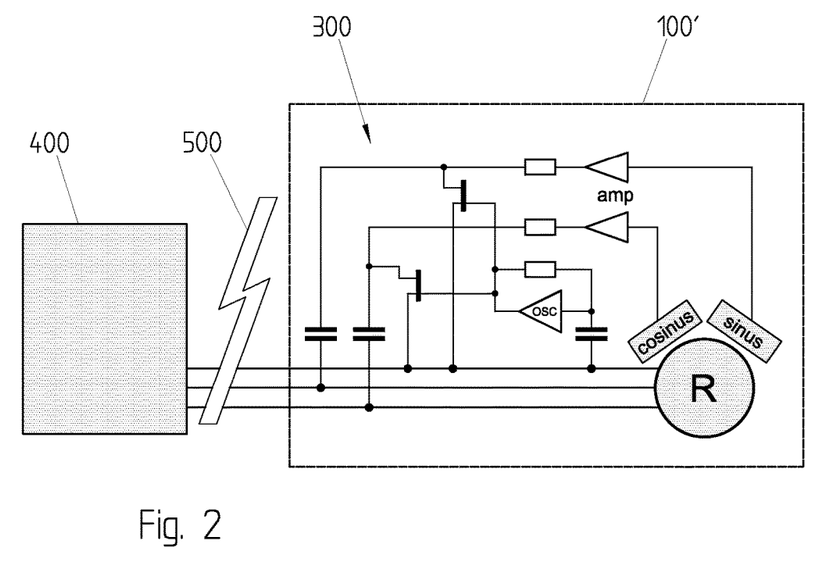
FIG. 2 illustrates an example of motor devoid of microprocessor that communicates the sine and cosine information concerning its position to a control electronic by amplitude modulation of a signal.

FIG. 2 illustrates an example of motor 100' devoid of microprocessor that comprises an electronic 300 for rotor position measurement R and that communicates the sine and cosine information concerning the position of the rotor R to an electronics control unit 400 by means of an amplitude modulated signal or any other type of modulated signal. In a preferred variant this signal has an oscillation frequency in the range 200 KHz-600 KHz, for example 400 KHz.

Figure 3A:
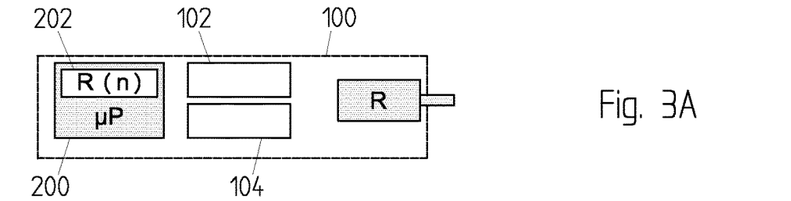
FIGS. 3A to 3F illustrate the steps of the method for recording the number of sterilizations of a motor equipped with a microprocessor, according to one embodiment of the invention.

The symbol 500 in FIGS. 1 and 2 indicates that during sterilization, a communication between the motor 100, respectively 100', and the electronic control unit 400 is no longer possible FIGS. 3A to 3F illustrate the steps of the method for recording the number of sterilizations of a motor 100 equipped with a microprocessor 200, according to one embodiment of the invention FIG. 3A shows a motor 100 in a rest state. It comprises a microprocessor 200, equipped with a register 202 arranged for holding a positive integer n, such as the number of sterilizations already performed, a sensor 102 and a storage element (or "flag") 104. In this context the storage element (or "flag") indicates an electronic component arranged for storing an information, preferably a digitized information, for example one or more bits indicating that an event (in this context, a sterilization) was held.

Figure 3B:
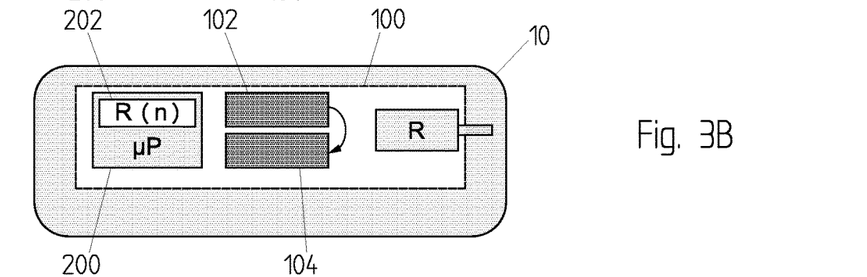
Figure 3C:
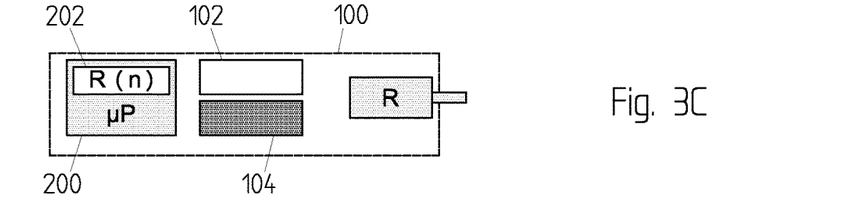
Figure 3D:
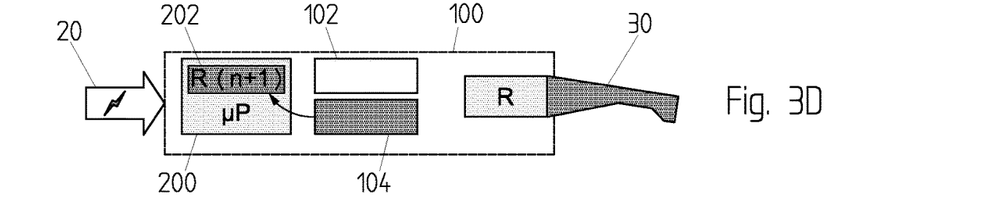
Figure 3E:
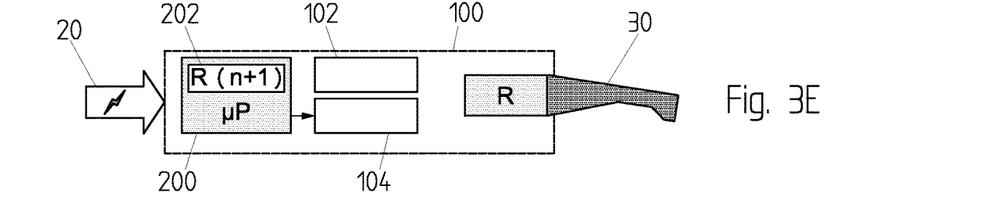

The motor 100 also comprises a rotor R suitable for driving a tool 30 illustrated in FIGS. 3D and 3E, for example a cutter.

The sensor 102 may be a temperature sensor and/or a pressure sensor: the temperature and pressure are physical quantities that can be used for detecting a sterilization. Indeed, when the motor is in operation, these two physical quantities show much lower values, for example an order of magnitude lower than those of the same motor during a sterilization, which avoids false sterilization detections.

In another variant the sensor 102 is a humidity sensor (hygrometer). However the information provided by such a sensor may in some cases be unreliable, especially if ambient moisture out of the sterilizing chamber is high, close to 100%, e.g. 90% or more.

In FIG. 3B the motor 100 is inserted into a sterilization chamber 10, for example an autoclave. The sensor 102 therefore senses the temperature and/or pressure in the sterilization chamber 10 and transmits this information to the storage element 104, as indicated by the arrow.

In a variant that information includes an indication that sterilization has taken place, as will be seen later.

In FIG. 3C the motor 100 is removed from the sterilization chamber 10, and the FLAG 104 maintains the information received during the step illustrated in FIG. 3B.

In FIG. 3D the motor 100 is turned on, as indicated schematically by the arrow 20. The FLAG 104 being lifted, the microprocessor 200 will increment the sterilization recorder from n to n+1 in the register 202 of the memory of the microprocessor 200.

In FIG. 3E the microprocessor 200 resets the FLAG information in the storage element 104.

Figure 3F:
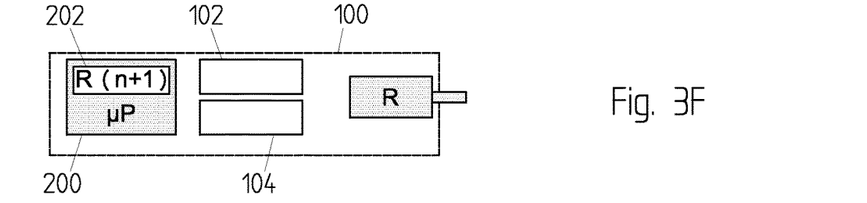

FIG. 3F shows a motor 100 ready for a new sterilization.

FIGS. 4A to 4F illustrate the steps of the method for recording the number of sterilizations of a motor 100 devoid of microprocessor that comprises an electronic 300 of FIG. 2.

Figure 4A:
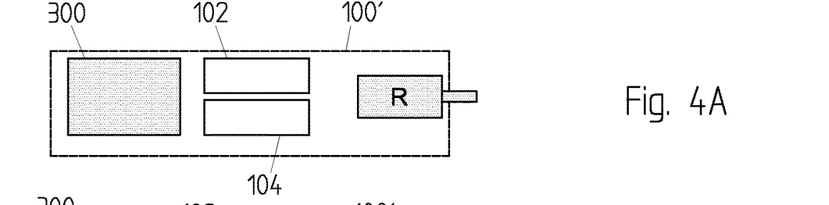
FIGS. 4A to 4F illustrate the steps of the method for recording the number of sterilizations of a motor devoid of microprocessor, according to another embodiment of the invention.

FIG. 4A illustrates a motor 100 in a rest state. The motor comprises an electronics 300 for measuring rotor position R, a sensor 102, a storage element (or "flag") 104 and the rotor R suitable for driving a tool 30, illustrated in FIGS. 4C and 4D, for example a strawberry. The considerations made on the sensor 102, on the storage element (or "flag") 104 and on the rotor R of FIG. 3A remain valid.

Figure 4B:
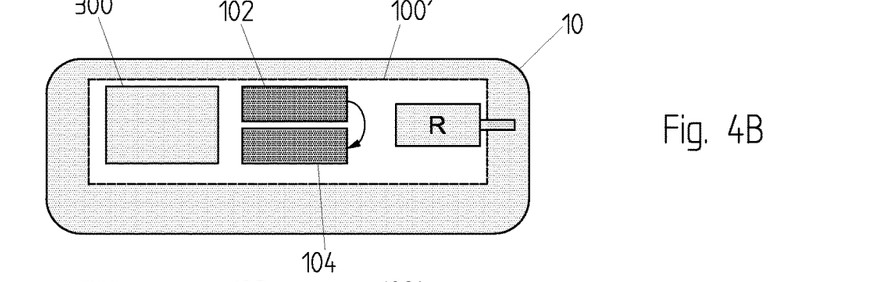

In FIG. 4B the motor 100' is inserted into a sterilization chamber 10, for example an autoclave. The sensor 102 therefore senses the temperature and/or pressure in the sterilization chamber 10 and transmits this information to the storage element 104, as indicated by the arrow.

Figure 4C:
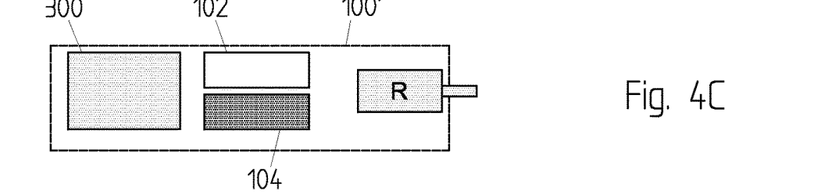

In FIG. 4C the motor 100' is removed from the sterilization chamber 10, and the FLAG 104 maintains the information received during the step illustrated in FIG. 4B.

Figure 4D:
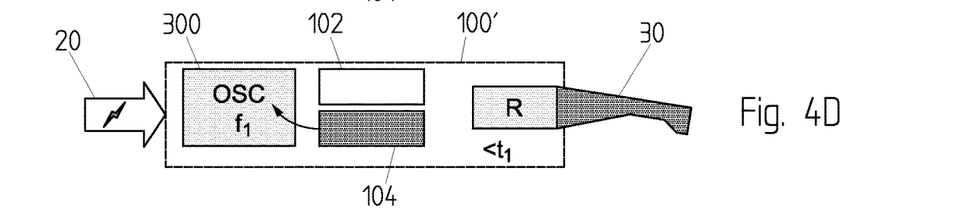

In FIG. 4D the motor 100' is turned on, as schematically indicated by the arrow 20. The FLAG 104 being lifted, the electronic oscillator 300 generates a signal at a first frequency f1 during a time span t1, allowing the electronic 400 to record a sterilization In a preferred variant the first frequency f1 is within the range 600 kHz-1000 kHz, for example 800 kHz, and the timespan t1 is between 1 ms and 200 ms, for example 10 ms or 100 ms. In general, the timespan t1 must be long enough for the electronic control unit 400 can determine that a sterilization has occurred and recorded it. The timespan t1 must take into account also the time to recharge a battery or a super-capacitor, which can be used as storage elements 104, as will be seen later.

Figure 4E:
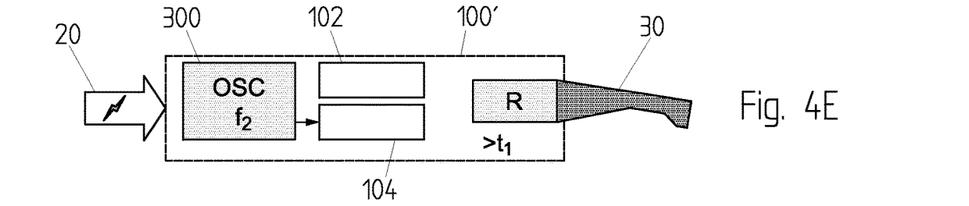

FIG. 4E illustrates the situation after the end of the timespan t1: the FLAG 104 is reset and the frequency of the modulated signal generated by the electronic oscillator 300 passes from f1 to another value f2 (second frequency), which in a preferred variant, is less than f1.

In a preferred variant the second frequency f2 is in the range 200 kHz-600 kHz, for example 400 kHz.

Figure 4F:
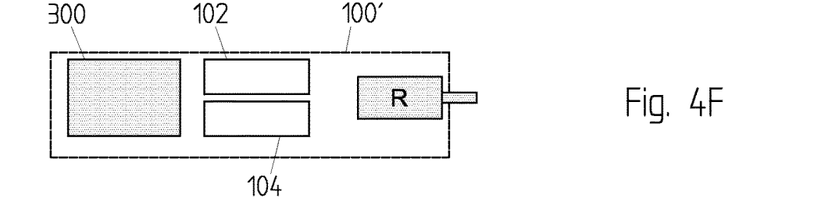

FIG. 4F shows a motor 100' ready for a new sterilization.

Figure 5A:
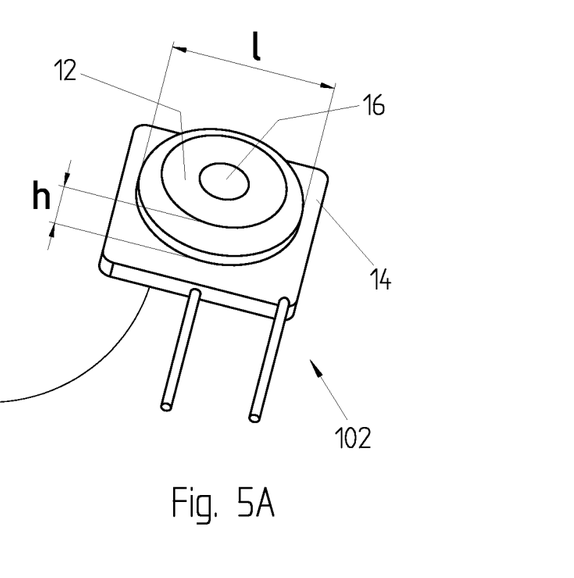
FIG. 5A illustrates an example of a pressure sensor for a motor according to an embodiment of the invention.

As discussed, the sensor 102 of the motor 100 or the motor 100' may be a pressure sensor. FIG. 5A illustrates an example of a pressure sensor 102. This pressure sensor comprises a metal piece 12, comprising a button-shaped portion. In a preferred variant this piece is made of copper, or in general any other conductive material. Button shown in FIG. 5A has a width 1 and a height h. In the illustrated embodiment, it has a circular cross section, but any other shape (square, rectangular, etc.) can be used.

In a preferred variant the width is less than 7 mm, for example 5 mm or 3 mm. In another variant the height h is less than 2 mm, for example equal to 1.5 mm or 1 mm.

In a variant the button-shaped metal piece 12 constitutes a protection from one or more electronic components during sterilization: in other words one or more electronic components can be placed in this button-shaped metal piece 12 and thus be protected from humidity, vapor, etc. generated during sterilization.

Preferably the metal piece 12 comprises a depression 16, shown in FIG. 5A.

Figure 5B:
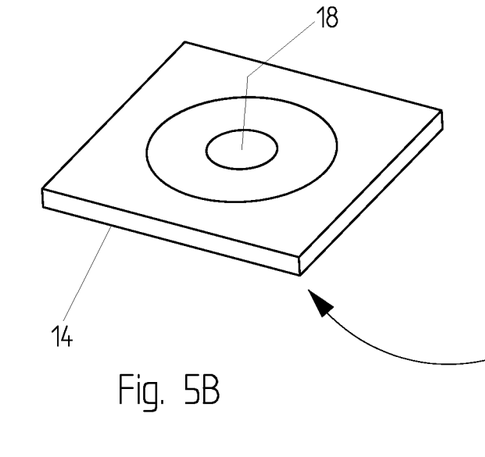
FIG. 5B illustrates an example of a printed circuit of the pressure sensor of FIG. 5A.

The metal piece 12 is arranged to be soldered to a printed circuit 14, or any type of non-conductive support, arranged to include conductive parts, including a pad or in general a conductive part 18, shown in FIG. 5B. In a preferred variant the conductive portion 18 is placed in correspondence of the depression 16.

Advantageously, the metal piece 12 includes a sealed volume of gas at atmospheric pressure, that is to say at ambient pressure (about 100 kPa), for example a volume of air. When a sterilization takes place, the pressure acts on the part 12 of the pressure sensor 102, so that this part 12, including its depression 16 comes into contact with the conductive portion 18 of the printed circuit 14.

The thickness of the piece 12 determines the value of the obtained contact pressure, which can vary between 0.1 bar (to a thickness of 0.1 mm of the piece 12) and 1.8 bar (a thickness of 0.25 mm of the piece 12).

In a preferred variant the piece 12 and the pad 18 of the printed circuit 14 undergo browning or any other suitable method for providing durability of electrical contacts.

In general, the pressure sensor 102 is a device arranged to allow an electrical contact when the sensed pressure is above a certain threshold, indicating that sterilization takes place.

Figure 6:
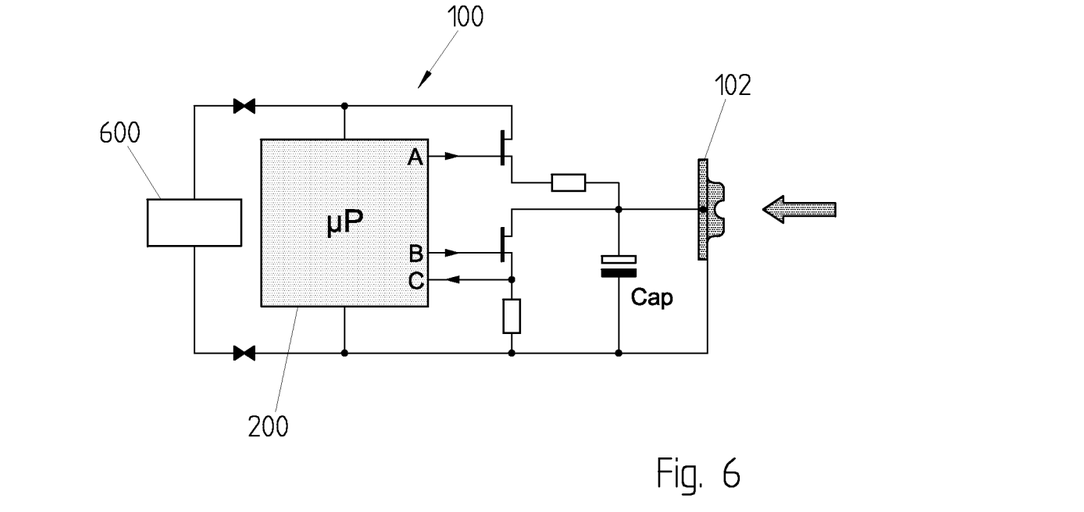
FIG. 6 illustrates an example of a motor equipped with microprocessor that comprises the pressure sensor of FIG. 5 and a super-capacitor.

FIG. 6 illustrates an example of a motor 100 equipped of a microprocessor 200 and comprising the pressure sensor 102 of FIG. 5 and a super-capacitor Cap.

In this context, the word "super capacitor" means a capacitor having a power density of between 1000 W/kg and 5000 W/kg and an energy density between 4 Wh/kg and 6 Wh/kg. In a preferred variant the super-capacitor used is the PAS3225P3R3113 marketed by Taiyo Yuden.

The super-capacitor Cap of FIG. 6 is an embodiment of the storage element 104 of FIGS. 3A to 3F. The super-capacitor Cap is systematically reloaded at every turn on of the motor 100 by the power supply 600 (for example providing a DC voltage of 3.3 V), activating the signal A microprocessor 200. When sterilizing (which is indicated by the arrow in correspondence with the pressure sensor 102), the super-capacitor Cap is discharged by the entry into contact of the pressure sensor 102. When the motor 100 is turned on, the B signal of the microprocessor 200 activates the measurement of the state of charge of the super-capacitor Cap, read from the C signal. If the super capacitor Cap is discharged, a sterilization occurred. The recharging of the super-capacitor is then performed Cap.

Figures 7, 8, 9, 10:
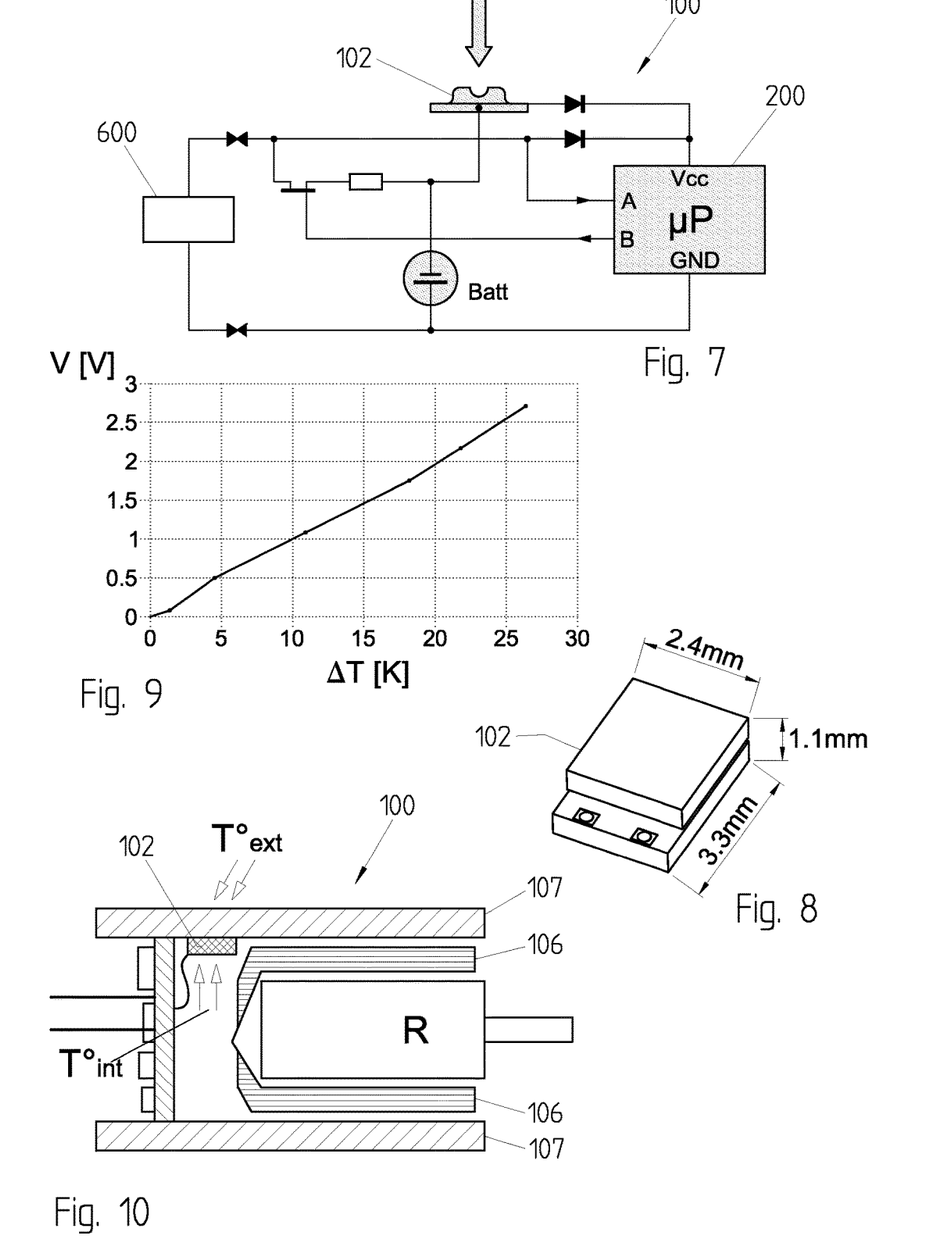
FIG. 7 illustrates an example of a motor equipped with microprocessor that comprises the pressure sensor of FIG. 5 and a battery.
FIG. 8 illustrates an example of a thermo-generator for a motor, according to an embodiment of the invention.
FIG. 9 shows a graph of the voltage generated by a thermo-generator as a function of a temperature difference.
FIG. 10 illustrates an example of a motor comprising a thermo-generator, according to an embodiment of the invention.

FIG. 7 illustrates an example of a motor 100 and equipped of microprocessor 200 including the pressure sensor 102 of FIG. 5. In this example the motor 100 also includes a battery Batt. The battery Batt of FIG. 7 is another variant of the storage element 104 of FIGS. 3A to 3F. In a variant of Batt battery is 12 pAh. In a preferred variant the battery Batt is CBC012-D5C-TR1 Battery Cymbet, which has dimensions of 5.0 mm×5.0 mm×0.9 mm. However any other battery having dimensions allowing its insertion into a medical instrument can be used.

In this variant the microprocessor 200 must have a power supply voltage in at least one mode of operation, for example in the low power mode of operation, compatible with the used battery Batt. For example, the microprocessor 200 may be an "ultra-low-power ARM Cortex-M3", for example STM32L151C6, which consumes only 9 uA in Low-Power Run, allowing the use of a 12 pAh battery.

The battery Batt of FIG. 7 supplies the microprocessor 200 only during the contact time of the pressure sensor 102 (50 ms is more than enough), signal A microprocessor 200 is "0" (respectively "1"), that increments the register of the microprocessor 200 containing the number of sterilizations.

When the motor 100 is running, thus under external pressure given by the power module 600 (providing for example a DC voltage of 3.3 V), the A signal is "1" (respectively "0"), the microprocessor 200 so recharge the battery Batt activating the B signal, but does not increment the register of the microprocessor 200 sterilizations.

The solutions illustrated on FIGS. 6 and 7 are reliable, simple and cheap.

As discussed, the sensor 102 of the motor 100 may alternatively be a temperature sensor. In another variant, a pressure sensor and a temperature sensor are both used.

FIG. 8 illustrates an example of a heat-generator for a motor 100 according to one embodiment of the invention. Its dimensions may be smalls, of the order of magnitude of those illustrated in FIG. 8, that is to say 2.4 mm×3.3 mm×1.1 mm Such thermo-generator operates the Seebeck effect, wherein the presence of a temperature difference, a potential difference appears at the junction of two materials, for example as illustrated in the graph of FIG. 9.

FIG. 10 illustrates an example of a motor 100 according to one embodiment of the invention, comprising a thermos-generator 102. A first wall of the thermos-generator 102 is connected to the carter 107 of the motor 100 to sense the outside temperature to the motor 100 Text, and a second wall of the thermo-generator 102 captures the internal temperature Tint of the internal cavity 105 of the motor 100, comprising a rotor R and the coil 106, schematically shown in FIG. 10.

During sterilization, the outside temperature Text rises rapidly to at least 120° C. On the other hand, the internal temperature Tint at the motor 100 progresses more slowly. In other words, there is a time during which the temperature difference external-internal (Text-Tint) is of the order of magnitude of tens of ° C.

The Embedded microprocessor 200 is programmed to detect if its power supply voltage come from an external source (motor is running) or from the thermo-generator 102 (motor in sterilization).

In a variant the minimum operating voltage of the microprocessor is about 2V, for example 1.8 V, so with reference to FIG. 9, a temperature difference of 20° C. during 50 ms is sufficient to generate such a voltage.

The solution of FIG. 10 is however more expensive than those of FIGS. 6 and 7.

In another variant, not illustrated, the microprocessor 200 of the motor 100 is continuously supplied even during its sterilization. However, this solution is cumbersome, because the size of the battery necessary for a sufficient monitoring time cannot fit inside of a motor for a medical device, in particular dental device, and is expensive.

Figure 11:
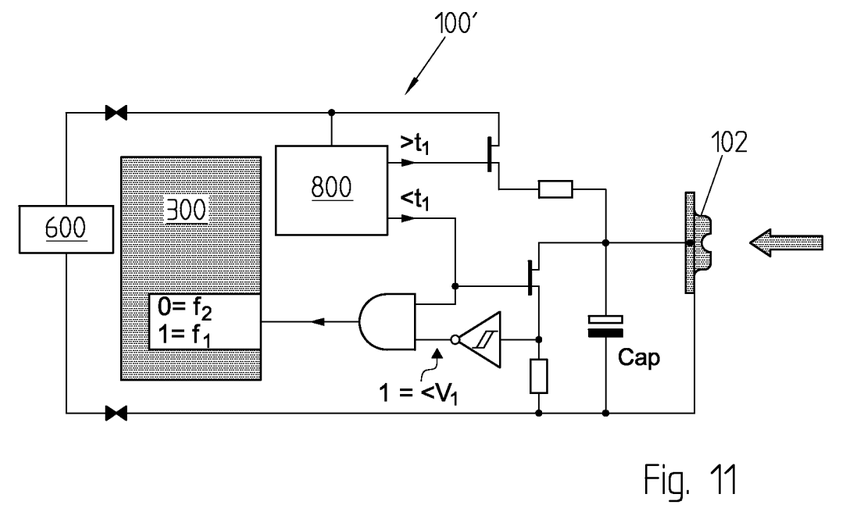
FIG. 11 illustrates an example of a motor devoid of microprocessor that includes the pressure sensor of FIG. 5 and a super-capacitor.

FIG. 11 illustrates an example of a motor 100' unequipped with microprocessor and comprising an electronic for measuring position 300, the pressure sensor 102 of FIG. 5 and a super-capacitor Cap.

When the motor is switched on by the power supply module 600 (providing for example a DC voltage of 3.3 V), a timer 800 is enabled. During a first timespan t1, for example 100 ms, if the voltage of the super-capacitor Cap is below a threshold V1, for example 200 mV, the oscillation frequency of the electronics measuring the position 300 emits a signal having a first frequency f1, for example 800 kHz, indicating to the electronic control unit 400, not shown, that a sterilization has occurred.

After the timespan t1, the transmission frequency passes to a second frequency f2, for example, 400 kHz and the super-capacitor Cap is put under load.

Figure 12:
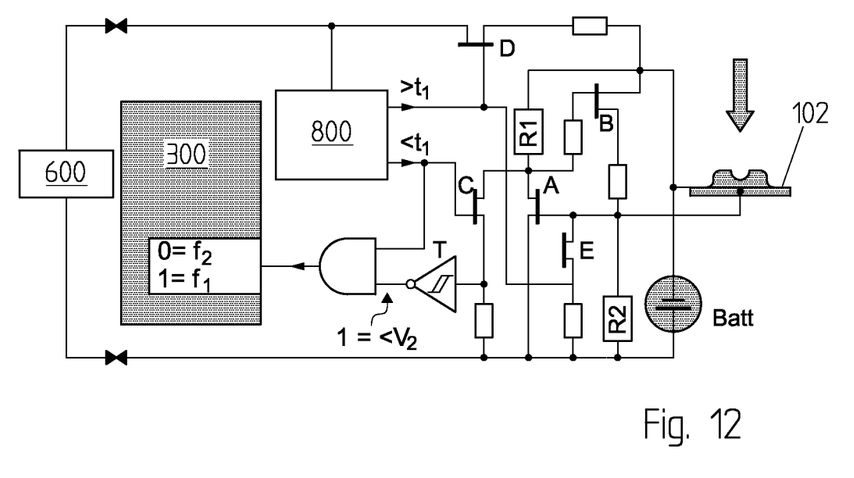
FIG. 12 illustrates an example of a motor devoid of microprocessor and including the pressure sensor of FIG. 5 and a battery.

FIG. 12 illustrates an example of a motor 100' unequipped of microprocessor and comprising an electronic for measuring position 300, the pressure sensor 102 of FIG. 5 and a battery Batt.

When the motor 100 is disconnected, waiting for sterilization, it has a charged battery Batt and all the non-conductive MOS transistors, including the transistor A by the resistor R2. The battery Batt is therefore subject to any charge.

At the time of sterilization, the pressure sensor 102 puts the gate of the transistor A to the battery voltage Batt. The drain voltage of the transistor A, named voltage [A]-[R1] in the following, falls to zero, which opens B (which in the illustrated variant is a PMOS) and maintains the transistor in conduction state even after disappearance of the contact provided by the pressure sensor 102 (thyristor effect). This stable state leads to a slow discharge of the battery Batt. However, this effect does not affect the sterilization FLAG indication that is given by a voltage [A]-[R1] lower than a threshold voltage V2, for example V2=1 V.

When the motor 100' is turned on again, during the timespan t1, for example 100 ms, the transistor C is conductive and if the voltage of the trigger T is less than V2, the frequency of the position signals is f1, for example 800 kHz.

After t1, the frequency drops to f2, for example 400 kHz and the transistor C is no more conductive. On the other hand, the transistor D becomes conductive and engages the recharging of the battery Batt. The transistor E also becomes conductive, which cancels the thyristor effect of the transistor A which is no more conductive and the cycle can start again.

The arrangement of the transistors A to E and of the resistors R1 and R2 of FIG. 12 is informative and should not be considered as limiting the present invention. Any other arrangement of transistors, resistors and other electronic components for the charging and discharging of the battery Batt as explained above is also possible.

According to an independent aspect of the invention, it is possible to detect whether a sterilization took place on the basis of the angular position of the motor in the sterilization chamber, by exploiting the fact that the motor has a generally cylindrical body and that the probability that it is placed in the sterilization chamber two or more times consecutively in the same angular position is very low or zero.

In other words, each time the motor is placed in the sterilization chamber, it assumes an angular position which most likely will be different from the angular position that the motor will assume when it is will placed anew in the sterilization chamber.

Indeed the motor is generally placed in a specific packet for this purpose, and then placed on a tray which is introduced into the interior of the sterilizing chamber, similar as a baking tray in an oven.

Once in the sterilization chamber, the motor axis is approximately horizontal in the vast majority of cases (99.9% of cases).

The motor is substantially balanced on its axis. In a variant it could be specifically improved if required to be balanced on its axis.

As discussed, the outer body of the motor is generally cylindrical, thus the motor in the sterilization chamber will almost never have the same angular position.

If the motor is not in the bag, it will probably roll and randomly rest against an edge of the tray, the horizontality of the latter is obviously not perfect, so the goal is to detect this angular change from case to case.

There are different possibilities to achieve an angular sensor that can detect the angular change of the motor from case to case, in order to record the number of sterilizations the same motor.

In a first variant we exploit a printed circuit which is generally present in a motor 100 with microprocessor, or 100' devoid of microprocessor. This printed circuit is generally perpendicular to the axis of the motor. In the context of this invention, the expression "axis of the motor" indicates the axis of the cylinder of the body of the motor.

If this circuit is not present in the engine, which is not generally the case, it is possible to add another printed circuit in the motor.

A side of this printed circuit may advantageously comprise a cover, preferably made of resilient synthetic material resistant to the sterilization (for example Rython). In another variant, the cover is metallic and coated with an insulating.

This cover is hermetically fixed on the printed circuit, and it defined a volume on its inside part.

In a preferred variant the cover is cylindrical, but it can also have other forms, provided that its shape is arranged so that it does not determine a unique position of the motor when placed in the sterilization chamber.

Before to fix the cover, in this volume is placed a quantity, for example a drop, of insulating material which has the feature of being solid at room temperature (for example 25° C.) and of passing to the liquid or gas state at the sterilization temperatures (120° C.-134° C.). A non limiting example of such a material is paraffin.

Inside this volume, before the fixing of the cover on the printed circuit, is also placed a quantity, for example a drop, of conductive material, for example water.

It is admit that air can be trapped in this volume.

The printed circuit area circumscribed within the cover comprises at least two crossing conductive contacts, for example golden contacts. In a variant these contacts are evenly distributed in the printed circuit area circumscribed within the cover. The number of such contacts determines the accuracy of the desired angular detection. These contacts are connected with ohmic measure elements located on the other face of the integrated circuit, opposite to the face that comprises the cover, and which generally comprises electronic components.

When the motor is placed in the sterilization chamber, the insulating material, for example the paraffin, melt and by gravity moves in the upper region of the volume defined by the cover, the water coming to position themselves in the lower region.

When the motor is removed from the sterilization chamber, the probability that the positioning of the paraffin once returned to the solid state is the same as the one it had before sterilization is very low or even zero.

It is thus a question of comparing a previous resistance value with the new one, and if there has been a change, it is possible for example to increment the corresponding memory of an embedded processor by one.

In another variant the motor may comprise a thermo-generator as that illustrated in FIG. 8, and a gyroscope. The thermo-generator is arranged as shown in FIG. 10. This thermo-generator is configured to generate, after the temperature difference Tint-Text a voltage required to turn on the gyroscope that can therefore sense the angular position of the motor in the chamber sterilization In another variant, the motor includes a box containing a movable magnet or a movable magnet piece. This box also includes paraffin or other insulating material that has the feature of being solid at room temperature (for example 25° C.) while to pass to the state of liquid or gas at the sterilization temperatures (120° C.-134° C.).

When the motor is not in the sterilization chamber and it is at ambient temperature, the insulating material, for example paraffin, is solid and keeps the movable part in a fixed position, by imprisoning it.

When the motor is placed in the sterilization chamber, the paraffin becomes liquid thereby releasing the movable part thus changes its position.

Once the motor outs from the sterilization chamber, a Hall sensor, a magneto resistive sensor or any other suitable sensor can determine the new position of the movable part, which is changed after the sterilization, and therefore may record a sterilization.

In another variant, the position sensor is a box comprising an unbalanced mass and arranged to be rotatable about the axis of the motor, and an insulating material which has the feature of being solid at room temperature (for example 25° C.) while to pass to the liquid or gas state at the sterilization temperatures (120° C.-134° C.), for example paraffin. In a variant the mass has the same shape as an oscillating mass of an automatic watch.

When the motor is not in the sterilization chamber and is at ambient temperature, the insulating material, for example paraffin, is solid and keeps the movable part in a fixed position, by imprisoning it.

When the motor is placed in the sterilization chamber, the paraffin becomes liquid thereby releasing the movable part that changes its position.

Once the motor outs from the sterilization chamber, the new position of the movable part, which is changed after the sterilization, can be determined by a proximity sensor. In a variant the movable part is made of metal, and the proximity sensor comprises a high frequency coil, for example at a frequency exceeding 500 kHz, for example, 1 MHz or more.

Although examples of the position sensors to determine the angular position of the motor have been described, it should however be understood that the invention is not limited to these examples, but includes other equivalent position sensors.

According to another independent aspect of the invention, the recording of the number of sterilization is performed by a passive RFID TAG of the motor that communicates with an RFID TAG connected to the sterilization chamber.

All variants described herein can also be used to record the number of sterilizations of a sensorless motor, using a temperature sensor and/or pressure and/or moisture and/or angular position described above. In this case the motor must contain the storage element 104 (FLAG) for storing the information sensed by one of these sensors. This information will be read and processed by the electronic control unit 400 once the sensorless motor is connected to the electronic control unit 400.

As discussed, a surgical instrument, in particular dental, includes a handpiece, for example an against-angle, which may be provided with a tool, for example a milling cutter—and a rotating motor that drives the tool. The handpiece and the motor may be two separate pieces and connected by appropriate interfaces or constitute a single piece.

In the case the handpiece and the motor constitute a single piece, all the considerations made below with respect to the motor also applies to the piece comprising both the handpiece and the motor.

In the case the handpiece and the motor are two separate pieces, the invention is not limited to the recording of the number of sterilizations of the motor of the medical device, in particular dental device, but it also allows to record the number of sterilizations of such a handpiece separated from the motor, as long as the handpiece comprises a temperature sensor and/or a pressure sensor and/or a humidity sensor and/or an angular position sensor.

The invention therefore also relates to a method for recording the number of sterilizations of a handpiece for a medical device, said hand piece comprising a temperature sensor and/or a pressure sensor and/or a humidity sensor and/or an angular position sensor that the handpiece has when it is placed in a sterilization chamber, said method comprising the following steps:

insertion of the handpiece in the sterilization chamber;

detection of the sterilization based on said temperature and/or of said pressure and/or said humidity and/or of said angular position sensed in said sterilization chamber by said temperature sensor and/or said pressure sensor and/or said humidity sensor and/or said angular position sensor.

If the handpiece separated from the motor comprises a storage element, the method may also comprise the following step:

Storing information that sterilization has occurred in said storage element

If the handpiece is separated from the motor, the invention also relates to a handpiece for a medical device, comprising a temperature sensor and/or a pressure sensor and/or a humidity sensor and/or angular position sensor that the hand piece has when it is placed in a sterilization chamber, each of said sensors being arranged to record the number of sterilization of the hand piece In a variant, the handpiece further comprises a storage element, for storing information that sterilization has occurred.

The invention claimed is:

1. Method for recording the number of sterilizations of a piece for a medical device, said piece being a motor and/or a handpiece, said piece comprising a storage element and a pressure sensor, said method comprising the following steps:

inserting said piece into the sterilization chamber;

detecting of a sterilization based on said pressure, wherein said step of detecting comprises storing of an information in said storage element, said information indicating that the sterilization has occurred; and wherein said step of storing the information comprises electrically discharging said storage element when a sensed pressure is above a predefined threshold.

2. Method according to claim 1, comprising the following steps:

extracting of said piece from said sterilization chamber;

power supplying of said motor by a power supply module.

3. Method according to claim 2, said motor comprising an electronic module comprising an oscillator, said method comprising the following steps:

recording of the sterilization by said electronic module by generating a signal at a first frequency during a timespan through said oscillator;

at the end of said timespan, cancellation of said information in said storage element, and generating a signal at a second frequency through said oscillator.

4. Method according to claim 3, said first frequency being in the range 600 kHz-1000 kHz, for example 800 KHz, said second frequency being in the range 200 kHz-600 kHz, for example 400 KHz, the said timespan being between 50 ms and 200 ms, for example 100 ms.

5. Method according to claim 2, said pressure sensor comprising a metal piece and a printed circuit, said metal piece being arranged to be soldered to said printed circuit; said metal piece comprising a volume of gas at atmospheric pressure, said method comprising the following step:

contacting the metal piece with a conductive portion of said printed circuit during an increase of the pressure outside said metal piece during a sterilization.

6. Method according to claim 5, said storage member comprises a super-capacitor connected to said pressure sensor, said method comprising the following step:

discharging said super-capacitor by contacting of the metal piece with the conductive portion of said printed circuit.

7. Method according to claim 6, said motor further comprising a microprocessor, the method comprising the following steps:

during the power supply of said motor, measuring of the state of charge of the super-capacitor by said microprocessor;

determining whether a sterilization took place on the basis of the state of charge;

recharging of the super-capacitor by said microprocessor.

8. Method according to claim 6, comprising the following steps:

during power supply of said motor, activating a timer of said motor;

If the voltage of the super-capacity during said timespan is smaller than a threshold, generating in said oscillator a signal at said first frequency, indicating that a sterilization occurred;

after said timespan, generating a signal at said second frequency and recharging the super-capacitor.

9. Method according to claim 7, said storage element comprising a battery connected to said pressure sensor, said method comprising the following step:

supplying said microprocessor only during the contacting of the metal piece with the conductive portion of said printed circuit.

10. Piece for a medical device, said piece being a motor and/or a handpiece, comprising: a pressure sensor arranged for sensing a pressure when said piece is placed in a sterilization chamber, said sensor being arranged to record the number of sterilizations of said piece; and a storage element, for storing information that the sterilization has occurred;

said pressure sensor being configured to electrically discharge said storage element when a sensed pressure is above a predefined threshold.

11. Piece according to claim 10, said piece comprising a motor, said motor further comprising a microprocessor, said microprocessor comprising a register, said register comprising a counter arranged to be incremented on the basis of said information of said storage element.

12. Piece according to claim 10, said pressure sensor comprising a metal piece and a printed circuit, said metal piece being arranged to be soldered to said printed circuit, said metal piece comprising a volume of gas at atmospheric pressure, the metal piece being arranged to come into contact with a conductive portion of said printed circuit during an increase of the pressure outside the metal piece during a sterilization; wherein the electrical circuit is laid out to provide an electrical contact discharging said storage element when a sensed pressure is above a predefined threshold.

13. Piece according to claim 12, said storage element comprising a super-capacitor connected to said pressure sensor.

14. Piece according to claim 12, said storage element comprising a battery connected to said pressure sensor.

15. Method for recording the number of sterilizations of a piece for a medical device, said piece being a motor and/or a handpiece, said piece comprising a microprocessor and a pressure sensor and/or a temperature sensor and/or a humidity sensor and/or an angular position sensor of said piece; the piece further comprising a storage element providing power supply, in particular a battery, that is operably connected to said pressure sensor and/or said temperature sensor and/or said humidity sensor and/or said angular position sensor; the method comprising the following steps:

inserting said piece into the sterilization chamber;

detecting of a sterilization based on said pressure and/or said temperature and/or said humidity and/or said angular position sensed in said sterilization chamber by said pressure sensor and/or temperature sensor and/or said humidity sensor and/or said angular position sensor;

wherein the storage element supplies said microprocessor only after the sterilization is detected, so that said microprocessor stores information that the sterilization has occurred.

16. Piece for a medical device, said piece being a motor and/or a handpiece, comprising a microprocessor and a pressure sensor and/or a temperature sensor and/or a humidity sensor and/or an angular position sensor arranged for sensing a pressure and/or a temperature and/or a humidity and/or an angular position when said piece is placed in a sterilization chamber;

the piece further comprising a storage element providing power supply, in particular a battery, that is operably connected to said pressure sensor and/or said temperature sensor and/or said humidity sensor and/or said angular position sensor;

said storage element being arranged to supply said microprocessor only when the sterilization is detected, the microprocessor being configured to store information that the sterilization has occurred.

* * * * *

UNITED STATES PATENT AND TRADEMARK OFFICE
CERTIFICATE OF CORRECTION

PATENT NO.       : 9,652,710 B2                                    Page 1 of 1
APPLICATION NO.  : 14/636559
DATED            : May 16, 2017
INVENTOR(S)      : Jean-Pierre Voillat It is certified that error appears in the above-identified patent and that said Letters Patent is hereby corrected as shown below:

In the Specification

Column 5, Line 63 please delete ""pAh"" and replace it with -- "µAh" --

Column 6, Line 7 please delete ""pAh"" and replace it with -- "µAh" --

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*